US008948343B2

United States Patent
Baumann et al.

(10) Patent No.: US 8,948,343 B2
(45) Date of Patent: *Feb. 3, 2015

(54) ARRANGEMENT AND METHOD FOR ACTIVE VIBRATION DAMPING WITHIN AN X-RAY RADIATOR

(75) Inventors: Berthold Baumann, Kastl (DE); Andreas Koerner, Elsendorf (DE); Christian Obst, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 238 days.

This patent is subject to a terminal disclaimer.

(21) Appl. No.: 13/472,596

(22) Filed: May 16, 2012

(65) Prior Publication Data
US 2012/0294412 A1     Nov. 22, 2012

(30) Foreign Application Priority Data
May 17, 2011    (DE) .......................... 10 2011 075 978

(51) Int. Cl.
| | |
|---|---|
| *H01J 35/00* | (2006.01) |
| *A61B 6/00* | (2006.01) |
| *G10K 11/178* | (2006.01) |
| *B06B 1/06* | (2006.01) |

(52) U.S. Cl.
CPC .............. *A61B 6/44* (2013.01); *A61B 6/4441* (2013.01); *G10K 11/1782* (2013.01); *B06B 1/06* (2013.01)

USPC .......................................................... 378/119

(58) Field of Classification Search
USPC .............. 378/4, 21, 119, 121, 122, 193, 196, 378/197, 204, 210; 700/280
See application file for complete search history.

(56) References Cited

U.S. PATENT DOCUMENTS

| | | | |
|---|---|---|---|
| 7,534,037 B2 | 5/2009 | Curtis | |
| 2005/0281391 A1* | 12/2005 | Luo et al. | 378/204 |
| 2013/0129036 A1* | 5/2013 | Baumann et al. | 378/4 |

FOREIGN PATENT DOCUMENTS

| | | |
|---|---|---|
| DE | 10 2008 047 814 A1 | 4/2010 |
| JP | 2003-245269 A | 9/2003 |

* cited by examiner

*Primary Examiner* — Jurie Yun
(74) *Attorney, Agent, or Firm* — Schiff Hardin LLP

(57) ABSTRACT

In an arrangement and method for active vibration compensation of an x-ray radiator, a counter-vibration generation unit is arranged within the x-ray radiator to reduce a vibration arising during operation of the x-ray radiator. The counter-vibration generating unit is engaged in an active connection with the x-ray radiator and generates a counter-vibration that is phase-shifted by 180 degrees relative to the operational vibration. Operational vibrations generated by the x-ray radiator can be directly reduced at the point of origin by the application of active counter-vibrations in the immediate proximity of the vibration generator. Additional vibration transmission to other system parts (for example a C-arm) is thereby reduced or prevented.

13 Claims, 2 Drawing Sheets

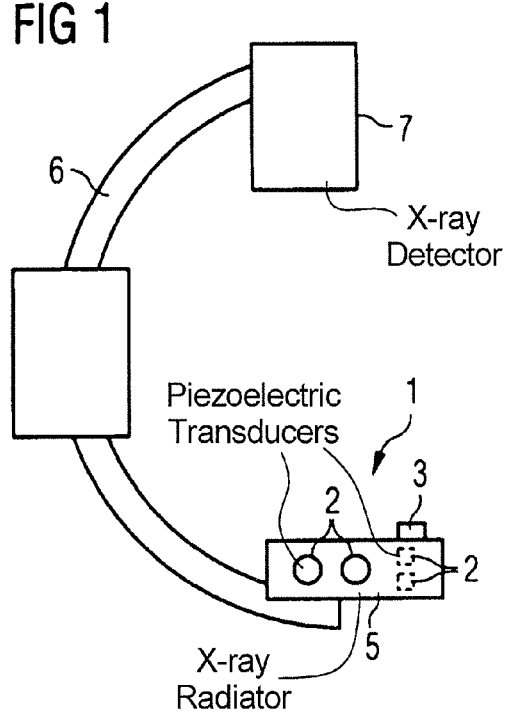
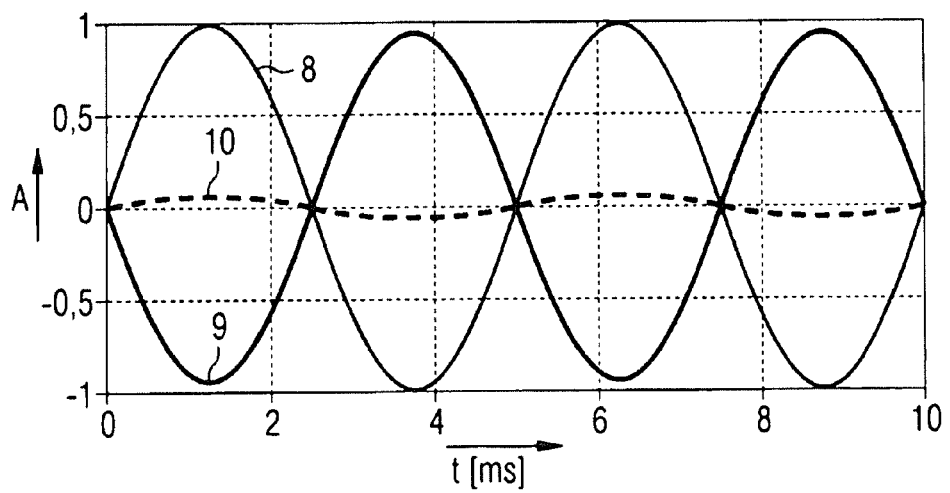

ARRANGEMENT AND METHOD FOR ACTIVE VIBRATION DAMPING WITHIN AN X-RAY RADIATOR

BACKGROUND OF THE INVENTION

1. Field of the Invention

The invention concerns an arrangement and a method for active vibration damping of an x-ray radiator with a counter-vibration acting on the x-ray radiator.

2. Description of the Prior Art

Two-dimensional or three-dimensional images of an examination region of a patient for diagnosis or therapy purposes are generated with tomography apparatuses. For example, three-dimensional slice images are generated with a computed tomography apparatus. The basic design of a computed tomography apparatus includes a gantry (support portal) with a stationary support frame in which a rotating frame is mounted such that it can rotate around an axis. An acquisition system that has an x-ray radiator and a detector arranged opposite the x-ray radiator is arranged on the rotating frame. Projections are acquired along a spiral path from a number of different projection directions by rotation of the rotating frame with simultaneous, continuous feed of a patient borne on a bed device in the direction of the system axis. Since 99% of the electrical energy used in the generation of x-ray radiation of the x-ray radiator is converted into thermal energy, the computed tomography apparatus has a cooling device in order to avoid an overheating of the electronic components.

In the operation of the mechanical and electrical components of the tomography apparatus, a noise level arises that is perceived as uncomfortable both by the patient and by the operator. For example, interfering structure-borne sound and airborne sound waves arise due to the rotation of the rotating frame, and/or due to the rotation of the anode within the x-ray radiator, and/or due to the operation of the cooling device. A resonance body that amplifies the noise amplitudes is formed by the casing (having) of the x-ray radiator. The patient is exposed to a particularly high noise level especially in the tunnel opening of the gantry through which the patient is shifted during the scanning.

An important aspect in the design of a tomography apparatus is therefore minimization of the interfering noise arising during operation of the tomography apparatus. There are two different approaches in order to suppress or minimize the propagation of interfering structure-borne and airborne sound waves in a tomography apparatus. One possibility is to reduce the interfering noise generation directly by optimization of the components causing the noise. For example, it would be possible to minimize the structure-borne sound wave propagation due to rotation of the rotating frame or rotation of the anode by the use of a noise-optimized rotating bearing. Such an optimization, however, is associated with high cost, and the achieved reduction of the interfering noise is normally insufficient.

Another possibility is to suppress the sound propagation by the use of noise damping mats. For example, the noise damping mats are adhered on the inside of the housing of the tomography apparatus to reduce the airborne noise propagation. The structure-borne sound propagation can also be minimized by use of corresponding passive damping materials at the contact points provided for mounting of the components. However, an effective reduction of the noise propagation is achieved only with a defined thickness of the damping material. The structural volume available for such damping is very limited, such that these measures are normally not sufficient in order to reduce the interfering noise to a desired level.

A tomography apparatus with a noise cancellation device and a method to reduce an interfering noise arising during operation of the tomography apparatus are specified in DE 102008047814 A1. The noise cancellation device has a control unit to provide a noise cancellation signal and a sound generation unit to convert the noise cancellation signal into an anti-noise signal that is shifted in terms of its phase by 180 degrees relative to the interfering noise. In this way the interfering noise can be effectively reduced during operation of the tomography apparatus.

Published Application US 2005/0281391 discloses a computed tomograph in which a vibration of the support frame is determined and, due to the oscillation, measures to remedy it are implemented.

SUMMARY OF THE INVENTION

An object of the present invention to provide a further arrangement and a further method to reduce interfering noise (system noise) of an x-ray system.

The basis of the invention is to compensate for the vibration of an x-ray radiator causing the interfering noise by intentionally generating a mechanical, antiphase counter-vibration. Cancellation occurs via interference or superimposition of vibration and counter-vibration.

The invention encompasses an arrangement with an x-ray radiator and with a counter-vibration generation unit arranged within the x-ray radiator to reduce vibration arising during operation of the x-ray radiator. The counter-vibration generation unit is engaged by an active connection with the x-ray radiator (for example with the rotating anode) and generates a counter-vibration that is phase-shifted by 180 degrees relative to the operational vibration. Vibrations generated by the x-ray radiator can be reduced directly at the point of origin by attach active counter-vibrators in immediate proximity to the vibration generator (source), so an additional vibration transfer to other system parts is reduced or prevented.

In an embodiment, the counter-vibration generation unit can be at least one electrodynamic transducer, a piezoelectric transducer or an electromotive transducer.

In a further embodiment, the arrangement can include a vibration measurement unit that determines the amplitude, the frequency and the phase position of the vibration.

Furthermore, the vibration measurement unit can be an acceleration sensor or a microphone, or can determine vibration parameters from a rotation speed of a rotating anode of the x-ray radiator.

The arrangement can, moreover, include a control unit that determines a counter-vibration signal from the determined amplitude, the frequency and the phase position, and controls the counter-vibration generation unit with these.

The invention also encompasses a tomography system with a vibration-countering arrangement as described above.

The invention also encompasses a method for active vibration compensation of an x-ray radiator, wherein a counter-vibration within the x-ray radiator is generated that is phase-shifted by 180 degrees relative to a vibration arising during operation of the x-ray radiator, and wherein the counter-vibration is applied to the x-ray radiator. The sum of vibration and counter-vibration should be minimal.

In an embodiment, the amplitude, the frequency and the phase position of the vibration are determined.

In a further embodiment, a counter-vibration signal is determined from the determined amplitude, the frequency and the phase position of the vibration, and the counter-vibration is controlled with the aid of the counter-vibration signal.

BRIEF DESCRIPTION OF THE DRAWINGS

FIG. 1 shows a C-arm with an x-ray radiator and a counter-vibration generation unit.

FIG. 2 is a graph of a vibration and a counter-vibration.

DESCRIPTION OF THE PREFERRED EMBODIMENTS

Figure 3:
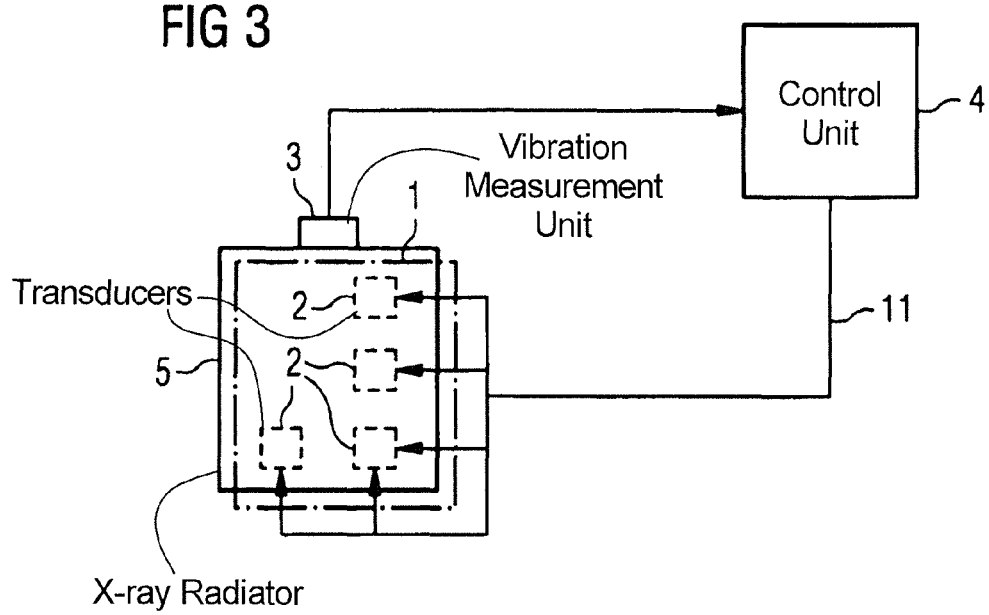
FIG. 3 is a block diagram of an x-ray tube with a counter-vibration generation unit in accordance with the invention.

FIG. 1 shows a portion of a C-arm x-ray system. A C-arm 6 is shown at whose two ends are arranged an x-ray radiator 5 and an x-ray detector 7 opposite one another. For example, the x-ray radiator 5 is set into vibration by a rotating rotary anode (not shown), which vibration is transferred to the C-arm 6 and leads to interfering sound waves. The curve 8 of the diagram of FIG. 2 shows the time curve of the vibration that is created. According to the invention, the amplitude, phase and frequency of the interfering vibration are now determined in all relevant directions with the aid of a vibration measurement unit 3 (an acceleration sensor, for example) engaged in an active connection with the x-ray radiator 5.

A counter-vibration of the same frequency and amplitude as the x-ray radiator 5, phase-shifted by 180°, is now charged within said x-ray radiator 5 with the aid of a counter-vibration generation unit 1 (that comprises four piezoelectric transducers 2 arranged in different directions, for example). By overlaying the interfering vibration and the counter-vibration charged in such a manner, it is achieved that the resulting vibration is minimized (or canceled out in the ideal case). Changes of the interfering vibration can be tracked with the aid of a control loop. The vibration parameters of interfering vibrations can also be determined via microphones in the space in which the C-arm apparatus is set up.

FIG. 2 shows a graph of the overlay principle according to the invention. The normalized amplitude A is shown depending on the time t in milliseconds within an interval of 10 ms. The curve 8 shows an interfering vibration of an x-ray radiator. The curve 9 shows a counter-vibration of identical frequency of a counter-vibration generation unit engaged in an active connection with the x-ray radiator. The counter-vibration 9 has nearly the same amplitude A as the interfering vibration 8. A resulting vibration according to curve 10 arises upon overlaying due to a 180° phase shift. It is apparent that the amplitude A of the resulting vibration 10 is nearly zero. This phenomenon is known as interference in wave theory.

FIG. 3 shows a block diagram of an arrangement according to the invention. Four transducers 2 of a counter-vibration generation unit 1 arranged within the x-ray radiator are connected with an x-ray radiator 5. A vibration measurement unit 3 engaged in an active connection with the x-ray radiator 5 detects the vibrations of the x-ray radiator 5 and relays the measurement value to the control unit 4. This determines the amplitude, the frequency and the phase position of the vibration and calculates from these a counter-vibration signal 11 that controls the counter-vibration generation unit 1. The four transducers 2 of the counter-vibration generation unit 1 apply the counter-vibration to the x-ray radiator 5 in different directions. The resulting vibration is thereby minimized.

Figure 4:
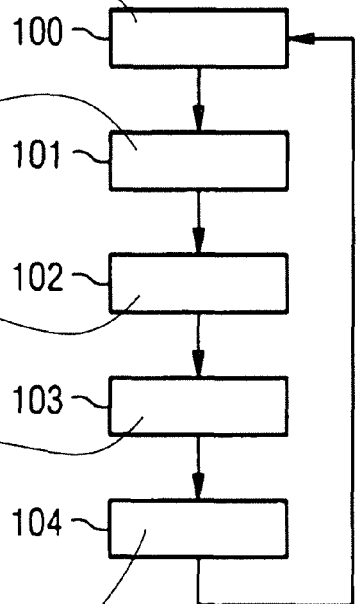
FIG. 4 is a flowchart of an embodiment of a method for active vibration compensation of an x-ray radiator in accordance with the invention.

FIG. 4 shows a flowchart of a method according to the invention for active vibration compensation of an x-ray radiator. In Step 100 the amplitude, the frequency and the phase position of an operational vibration of an x-ray radiator are determined. In the subsequent Step 101, from this a counter-vibration signal is determined that controls the amplitude, the frequency and the phase position of a counter-vibration in Step 102. In Step 103 the counter-vibration is generated using the counter-vibration signal, and in Step 104 the x-ray radiator is charged from the inside. The method proceeds in a control loop that takes changes into account.

Although modifications and changes may be suggested by those skilled in the art, it is the intention of the inventor to embody within the patent warranted hereon all changes and modifications as reasonably and properly come within the scope of his contribution to the art.

We claim as our invention:

1. An x-ray radiator comprising:
   a radiator housing;
   a plurality of components within said radiator housing, said plurality of components being configured to operate to generate x-rays, and at least one of said components causing operational vibration during operation of said at least one component; and
   a counter-vibration generation unit in said radiator housing configured to at least reduce said operational vibration by an active connection with at least one of said radiator housing and at least one of said components and by generating a counter-vibration that is phase-shifted by 180° with respect to said operational vibration.

2. An x-ray radiator as claimed in claim 1 wherein said counter-vibration generation unit comprises at least one electrodynamic transducer.

3. An x-ray radiator as claimed in claim 1 wherein said counter-vibration generation unit comprises at least one piezo-electric transducer.

4. An x-ray radiator as claimed in claim 1 wherein said counter-vibration generation unit comprises at least one electromotive transducer.

5. An x-ray radiator as claimed in claim 1 comprising a vibration measurement unit that measures an amplitude, a frequency and a phase position of said operational vibration.

6. An x-ray radiator as claimed in claim 5 wherein said vibration measurement unit comprises at least one of an acceleration sensor and a microphone.

7. An x-ray radiator as claimed in claim 5 wherein said at least one of said components that causes said operational vibration is a rotating anode, and wherein said vibration measurement unit is configured to determine said amplitude, frequency and phase position of said operational vibration from a rotational speed of said rotating anode.

8. An x-ray radiator as claimed in claim 5 comprising a control unit configured to determine a counter-vibration signal from said amplitude, said frequency and said phase position determined by said vibration measurement unit and to operate said counter-vibration generation unit to cause said counter-vibration generation unit to generate said counter-vibration dependent on said counter-vibration signal.

9. A tomography system comprising:
   an x-ray radiator and a radiation detector mounted for rotation around a system axis to generate tomographic data by irradiating an examination subject with x-rays and detecting the x-rays attenuated by the subject; and
   said x-ray radiator comprising a radiator housing, a plurality of components within said radiator housing, said plurality of components being configured to operate to generate said x-rays, and at least one of said components causing operational vibration during operation of said at least one component, and a counter-vibration generation unit in said radiator housing that at least reduces said operational vibration, said counter-vibration generation unit being in active connection with at least one of said radiator housing and at least one of said components and configured to generate a counter-vibration that is phase-shifted by 180° with respect to said operational vibration.

10. A tomography system as claimed in claim 9 comprising a C-arm on which said x-ray radiator and said radiation detector are mounted for rotation around said system axis.

11. A tomography system as claimed in claim 9 comprising a gantry in which said x-ray radiator and said radiation detector are mounted for rotation around said system axis.

12. A method for active vibration compensation of an x-ray radiator, comprising:
   operating an x-ray radiator and, during operation of said x-ray radiator, generating operational vibration;
   in said x-ray radiator, generating a counter-vibration that is phase shifted by 180° relative to said operational vibration; and
   applying said counter-vibration to said x-ray radiator with a sum of said operational vibration and said counter-vibration being minimal.

13. A method as claimed in claim 12 comprising determining an amplitude, frequency and phase of said operational vibration and generating said counter-vibration dependent on the determined amplitude, frequency and phase of said operational vibration.

* * * * *